(12) United States Patent
Nore et al.

(10) Patent No.: US 6,855,524 B1
(45) Date of Patent: Feb. 15, 2005

(54) METHOD FOR PRODUCING EXOPOLYSACCHARIDES

(75) Inventors: Olivier Nore, Azay-sur-Cher (FR); Jean-Luc Simon, Lille (FR)

(73) Assignee: Danisco USA Inc., New Century, KS (US)

( * ) Notice: Subject to any disclaimer, the term of this patent is extended or adjusted under 35 U.S.C. 154(b) by 396 days.

(21) Appl. No.: 10/070,632

(22) PCT Filed: Sep. 6, 2000

(86) PCT No.: PCT/FR00/02452

§ 371 (c)(1),
(2), (4) Date: Jul. 2, 2002

(87) PCT Pub. No.: WO01/18226

PCT Pub. Date: Mar. 15, 2001

(30) Foreign Application Priority Data

Sep. 7, 1999 (FR) .............................. 99 11176

(51) Int. Cl.⁷ ................................................. C12N 5/00
(52) U.S. Cl. ........................ 435/101; 435/104; 424/115; 424/116; 424/119; 424/120; 424/121; 424/122
(58) Field of Search ................................ 424/115, 116, 424/119, 120, 121, 122; 435/101, 104

(56) References Cited

PUBLICATIONS

Roukas Triantafyllos et al.: "Evaluation of carob pod as a substrate for pullulan Production by *Aureobasidium pullulans*." Applied Biochemistry and Biotechnology, vol. 55, No. 1, Oct. 1995, pp. 27–44, XP000915013, ISSN: 0273–2289.

Roseiro J C et al.: "Batch and Fed–Batch Cultivation of Xanthomonas–Campestris in Carob Extracts" Lebensmittel–Wissenschaft & Technologie, vol. 25, No. 3, 1992, pp. 289–293, XP000922972, ISSN: 0023–6438.

International Search Report.

*Primary Examiner*—Jean C. Witz
(74) *Attorney, Agent, or Firm*—Fay, Sharpe, Fagan, Minnich & McKee, LLP

(57) ABSTRACT

The invention concerns a method for producing exopolysaccharides by fermenting micro-organisms characterised in that it consists in carrying out the fermentation in a nutrient medium comprising at least a source of carbon available to the micro-organisms and at least a source of nitrogen, said source being derived from a fraction of carob seed.

19 Claims, No Drawings

METHOD FOR PRODUCING EXOPOLYSACCHARIDES

This application is an application under 35 U.S.C. Section 371 of International Application Number PCT/FR00/02452 filed on Sep. 6, 2000.

The present invention relates to a process for the production of exopolysaccharides by fermentation by means of microorganisms. More specifically, the invention relates to a process for the production of exopolysaccharides by fermentation of microorganisms in a nutrient medium containing at least one carbon source assimilable by the microorganisms and at least one organic nitrogen source deriving from a leguminous plant having a high content of proteins.

In the context of the present invention, the term exopolysaccharide denotes the polysaccharides produced by microorganisms.

The exopolysaccharides of high molecular weight are increasingly used in numerous industrial applications for their thickening, viscosifying, emulsifying, stabilizing properties in especially aqueous media. Thus, xanthan gum, because of its exceptional rheological properties, is used in areas as varied as the building industry, painting, paper, the textile industry, cosmetics, food, agriculture, water treatment, drilling, oil recovery etc.

These exopolysaccharides have high molecular weights, most often greater than $1 \times 10^6$ g/mol (measured by gel permeation), and are formed of units of glucose, mannose, galactose, rhamnose, glucuronic acid, mannuronic acid, guluronic acid, optionally with acetate and pyruvate derivatives. Their particular structure and their properties are described, for example, in the work Industrial Gums—Whistler—2nd Edition—Chapters XXI–XXIII (1973).

The exopolysaccharides are advantageously produced by aerobic culture of microorganisms in an aqueous nutrient medium.

Xanthan gum is produced by bacteria of the genus *Xanthomonas*. The exopolysaccharides of the same type can be produced by a great variety of microorganisms including, among the most well known, those of the genus *Agrobacterium, Arthrobacter, Alcaligenes* (Succinoglycan), *Pseudomonas* (Levan), *Rhizobium, Sclerotium* (Scleroglucan).

The aqueous nutrient medium normally comprises, apart from various growth elements, a carbon source and a nitrogen source. In the industrial fermentations, the choice of the carbon source and/or of the nitrogen source is at the same time based on its availability, on its cost and on its ability to allow high productivities.

In certain industries, such as, for example, the food or cosmetic industry, additional constraints operate. In these areas, the carbon and nitrogen sources must, in addition, be chosen so as to obtain exopolysaccharides satisfying the organoleptic, sensory and visual requirements sought.

Among the carbon and/or nitrogen sources customarily used, it is not easy to find sources which at the same time meet all the abovementioned requirements.

For example, in the case where the microorganism is not capable of consuming all of the nitrogen source, insoluble residual products remain at the end of fermentation which on the one hand make the medium favorable to the development of contaminant strains which are able to degrade the must before separation of the exopolysaccharide, and on the other hand risk coloring the exopolysaccharide during possible sterilization and clarification heat treatments. In certain fermentation processes, to remedy this disadvantage, it is proposed to use enzymes. Others employ filtration and/or centrifugation steps. Whatever the process of elimination of insoluble residual products at the end of fermentation, an increased cost of production results therefrom.

Certain carbon and/or nitrogen sources have the disadvantage of considerably prolonging the fermentation cycle involving, especially, the contamination and thus the degradation of the must before separation of the exopolysaccharide, and the loss of production.

The nature of the nitrogen source is particularly important when it is sought to obtain an exopolysaccharide having good organoleptic, sensory and visual properties. It is also responsible for the good productivity of the exopolysaccharide.

It has been noted that certain sources deriving from a fraction of the seed of certain leguminous plants, such as the carob bean, was an organic nitrogen source of particular interest in the fermentation of microorganisms. These fractions have proved to satisfy all of the abovementioned requirements.

Among the fractions deriving from the carob bean, those advantageously having a high content of proteins give particularly interesting results, especially in terms of productivity. On "standard" media such as those mentioned, for example, in the work Industrial Gums—Whistler—2nd Edition—Chapters XXI–XXIII (1973), for control fermentations, the productivities are of the order of 0.3 to 0.4 g/(kg.h); for fractions deriving from the carob bean, this productivity is greater than 0.4 g/(kg.h).

The aim of the present invention is to propose a process for production of exopolysaccharides by fermentation of microorganisms, which is simple and economical.

Another aim of the invention is to propose a process for production of exopolysaccharides by fermentation of microorganisms which avoids the problems of contamination explained above.

Thus, the invention relates to a process for production of exopolysaccharides by fermentation of microorganisms, characterized in that the fermentation is carried out in a nutrient medium containing at least one carbon source assimilable by the microorganisms and at least one organic nitrogen source, said source deriving from a fraction of the carob bean.

Other advantages linked to the choice, especially, of the nitrogen source, are the reduction of the time of the fermentations, the suppression of insoluble residual products at the end of fermentation and an improved productivity.

In addition, this process allows an exopolysaccharide to be obtained having good organoleptic, sensory and visual properties.

Furthermore, the rheological properties of the exopolysaccharide obtained by this process are preserved and even improved in certain cases.

The process of the invention is capable of being applied to the production of any exopolysaccharide by fermentation by means of microorganisms. Numerous microorganisms such as bacteria, yeasts, fungi, algae, are capable of producing exopolysaccharides. It is possible to mention, among others:

bacteria belonging to the genus *Xanthomonas* and more particularly to species described in Bergey's Manual of Determinative Bacteriology (8th edition—1974—Williams N. Wilkins Co. Baltimore) such as *Xanthomonas begoniae, Xanthomonas campestris, Xanthomonas carotae, Xanthomonas hederae, Xanthomonas incanae, Xanthomonas malvacearum, Xanthomonas papavericola, Xanthomonas phaseoli, Xanthomonas pisi, Xanthomonas vasculorum, Xanthomonas vesicatoria, Xanthomonas vitians, Xanthomonas pelargonii;* bacteria belonging to the genus *Arthrobacter* and more particularly the species *Arthrobacter stabilis, Arthrobacter viscosus;* bacteria belonging to the genus *Erwinina;* bacteria belonging to the genus *Azotobacter* and more particularly the species *Azotobacter indicus;* bacteria to the genus *Agrobacterium* and more particularly the species *Agrobacterium radiobacter, Agrobacterium rhizogenes, Agrobacterium tumefaciens;* bacteria belonging to the genus *Alcaligenes* and more particularly *Alcaligenes faecalis;* bacteria belonging to the genus *Pseudomonas* and more particularly *Pseudomonas methanica;* bacteria belonging to the genus *Corynebacterium;* bacteria belonging to the genus *Bacillus* and more particularly *Bacillus* polymyxa;

fungi belonging to the genus *Sclerotium* and more particularly to the species *Sclerotium glucanicum, Sclerotium rolfsii* or *Plectania occidentalis;* fungi belonging to the genus *Aspergillus* and more particularly to the species *Aspergillus itaconicus, Aspergillus terreus;* yeasts belonging to the genus *Hansenula* such as the species *Hansenula capsulata.*

Preferably, the microorganism is a bacterium of the genus *Xanthomonas* and more particularly of the species *Xanthomonas campestris.*

The invention principally relates to a process for production of exopolysaccharides by fermentation of microorganisms, characterized in that the fermentation is carried out in a nutrient medium containing at least one carbon source assimilable by the microorganisms and at least one organic nitrogen source, said source being derived from a fraction of the carob bean.

The carob tree produces a fruit formed of two parts, the pod and the bean. The carob bean, and more particularly the endosperm fraction of this bean, is already widely developed under the name "carob bean gum". Closely related to this endosperm fraction is the germ, which is a by-product obtained in large quantities during the isolation of the carob bean gum.

Among the different fractions of the carob bean, it turns out that all those having a high content of proteins were more particularly suited to the process of the present invention.

Thus, the fraction of the carob bean advantageously has a protein content of at least 45%, preferably of at least 50%, and more preferentially of at least 60%, by weight with respect to the dry weight of the dry material.

The protein content is calculated from the measurement of the nitrogen liberated by combustion at 950° C. under oxygen and measured by conductivity in a stream of helium. The apparatus used is a LECO FP 428.

These proteins are formed as much of essential amino acids as of nonessential amino acids.

A particular embodiment of the invention consists in employing fractions of the carob beans whose proteins advantageously have a high content of arginine, of glutamine and/or of glutamic acid, and of lysine.

In this particular embodiment, the arginine content is advantageously between 9 and 20%, and preferably between 12 and 14%, weight/weight with respect to the total of amino acids.

In the same fashion, the content of glutamine and/or glutamic acid is advantageously between 18 and 30%, preferably between 22 and 27%, weight/weight with respect to the total of amino acids.

The content of lysine is advantageously between 18 and 30%, preferably between 12 and 14%, weight/weight with respect to the total of amino acids.

The content of amino acids is determined by methods which are conventional and known to the person skilled in the art.

Apart from the proteins, the fractions can likewise contain lipids. The exopolysaccharides produced by fermentation of microorganisms in a nutrient medium containing at least one organic nitrogen source derived from a fraction of the carob bean containing lipids more particularly see their organoleptic, visual and sensory properties markedly improved. These lipids likewise prevent the foaming in the preculture phases.

Advantageously, the content of lipids in said fractions is at least 4%, advantageously at least 5%, and even more advantageously varies between 7 and 15% by weight with respect to the dry matter.

The content of lipids is reduced to that of the total dry matter. It is determined by extraction with hexane in a Soxhlet extractor. The operating mode is as follows:

exactly about 10 g of carob germ flour, say E grams, are weighed into the cartridge of the extractor, sealed with a plug of absorbent cotton;

150 ml of hexane are introduced into a 250 ml round-bottomed flask, previously tared (P0 grams);

the mixture is extracted for about 6 hours;

the solvent is evaporated using a rotary evaporator and the drying of the residue is completed in an oven at 105° C. for 1 hour;

after cooling in a desiccator, the round-bottomed flask containing the residue, say P1 grams, is weighed.

The content of fatty matter and thus of lipids is determined according to the following formula:

$$\text{Content of fatty matter }(\%)=100\times(P1-P0)/E$$

Among the characteristic compounds present in these lipids, it is especially possible to mention palmitic, stearic, oleic and linoleic acids.

Beside the proteins and the lipids, the fractions of the carob bean can also contain carbohydrates.

According to a particular embodiment of the invention, said fraction is the germ of the carob bean.

In this embodiment, said fraction is first freed of its endosperm fractions according to the known conventional methods.

The fraction of the carob bean used can preferably be in the form of a flour. The flour is obtained by conventional means of grinding such as grinding in mills of the type:

cylinder mills for flours of average granulometry 100 mesh type, that is to say a flour having at most 1% by mass of particles of greater than 80 mesh and at most 10% by mass of particles of less than 200 mesh;

pin mills for flours of finer granulometry:

200 mesh type, that is to say a flour not having particles of greater than 80 mesh and having at most 60% by mass of particles of less than 200 mesh, and 175 mesh type, that is to say a flour having at most 1% by mass of particles of greater than 80 mesh and at most 75% by mass of particles of less than 200 mesh.

The flour can be used as it is or after treatment by suitable enzymes such as, for example, alkaline, acid and/or neutral proteases; lipases; phytases; alkaline, acid and/or neutral phosphatases; amylases. The treatment by the enzymes is carried out by conventional and known methods.

The granulometry of said flour can fluctuate between 10 and 150 microns. In the case of treated flours, this granulometry is more particularly from 20 to 60 microns, preferably from 30 to 50 microns.

The granulometry measurements can be carried out by the laser granulometry technique, with the aid of a MALVERN granulometer, marketed by Malvern Instruments S.A.

It is likewise possible to envisage the use of the fraction of the carob bean as it is, that is to say after separation of the endosperm in the form of platelets, or even in the form of an aqueous predispersion or presuspension.

Although the invention is described for the carob bean, it can likewise apply to other leguminous plants such as, for example, guar, cassia, tara. These leguminous plants are mentioned in an indicative and nonlimiting capacity.

In another particular embodiment of the invention, the fermentation takes place with a mixture of organic and inorganic nitrogen sources.

In this case, the inorganic nitrogen source can be chosen from the ammonium or sodium nitrates, the ammonium phosphates or sulfates, magnesium sulfate, potassium or sodium sulfate, on their own or as a mixture.

The concentration of organic and optionally inorganic nitrogen sources in the fermentation medium is between 1 and 80 g/l, preferably between 3 and 50 g/l, and more preferentially between 5 and 30 g/l.

The fermentation medium likewise contains a source of carbon assimilable by the microorganisms.

As constitutive carbon source of the fermentation medium, it is possible to mention glucose, sucrose, fructose, galactose, trehalose, mannose, melobiose, raffinose, maltotriose, maltose, lactose, lactulose, methyl-β-galactopyranoside, methyl-α-qalactopyranoside, cellobiose, gentobiose, methyl-β-D-glucopyranoside, methyl-α-D-glucopyranoside, esculin, ribose, arabinose, xylose, palatinose, rhamnose, fucose, melezitose, D(+) arabitol, L(−) arabitol, xylitol, dulcitol, tagatose, glycerol, myoinositol, mannitol, maltitol, turanose, sorbitol, adonitol, lyxose, erythritol advantageously hydrolyzed starch, starch hydrolyzates, mixtures of these sugars, and mixtures comprising at least one of these sugars. Glucose and sucrose are the preferred sugars.

The concentration of assimilable carbon source is between 1 and 100 g/l, and preferably between 15 and 80 g/l.

The fermentation medium can, in addition, contain oligoelements such as traces of mineral salts, such as sulfates, chlorides of iron, of calcium, of manganese, of magnesium, of sodium, of potassium, of nickel, of cobalt, of copper, of zinc or a mixture thereof, as well as vitamins, nucleotides and/or other conventional additives such as pH control agents and antifoam agents.

The process for production of exopolysaccharides according to the invention by fermentation of microorganisms can optionally be carried out in the presence of enzyme(s) such as alkaline, acid and/or neutral proteases; polysaccharases; amidases; peptidases, amyloglucosidases, phosphatases; phytases.

However, one of the important advantages of the process according to the invention resides in the fact that it is possible to carry out the fermentation of the microorganisms in the absence of enzyme. It has quite surprisingly been noted that in the absence of enzyme, neither the time nor the productivity of the fermentation process were affected. In addition, the suppression of enzyme did not involve an accumulation of insoluble and undissolved residual products at the end of fermentation which can render the medium favorable to the development of contaminating strains which are able to degrade the must before separation of the exopolysaccharide.

The pure culture of the microorganisms can be carried out in the conventional manner. The person skilled in the art, as a function of the microorganism, will be in a position to choose the conditions, especially the temperatures and times of incubation, and the nature of the maintenance medium of said microorganism.

For the conservation of the microorganism, it is preferable to provide for at least one preculture step. Preculture is understood as meaning a step which consists in developing and in multiplying the bacterial strain, without production of exopolysaccharide.

The microorganism is introduced into the fermentation medium in known manner by itself with the aid of inocula or intermediate cultures.

The fermentation can be carried out at pressures of between 0 and 4 bar.

It is possible to carry out the fermentation at a temperature of between 15 and 100° C., preferably between 25 and 80° C., and more particularly between 25 and 35° C.

The pH of the fermentation medium can vary between 5 and 9, and preferably between 6 and 8. The pH can be adjusted, according to the case, with a base such as sodium hydroxide, potassium hydroxide or ammonia, or with an acid such as sulfuric acid, phosphoric acid, hydrochloric acid or nitric acid.

The fermentation medium, placed in a tank or a fermentation vessel, can be advantageously subjected to stirring and to aeration. This stirring can be conducted, for example, by means of a reciprocating stirrer, a gyratory stirrer, one or more stirring moving body(ies) or a bubble column. The fermentation time is customarily greater than 30 hours, but generally between 40 and 100 hours.

The productivity is measured as a function of the quantity of exopolysaccharide produced, expressed in grams, with respect to kg of must, per hour of fermentation. With the process of the invention, an improvement in productivity of 3 to 15%, and preferably of 5 to 10%, has been observed.

After completion of the fermentation, the exopolysaccharide can be recovered from the must and purified according to the known methods such as filtration, concentration, crystallization or extraction by solvents.

The invention likewise covers the exopolysaccharides obtained or capable of being obtained by the process. It more particularly covers xanthan gum produced by the process of the invention.

The xanthan gum obtained according to the process of the invention, in 1% aqueous solution in distilled water, has a high transparency, that is to say of the order of 70 to 95% or even of the order of 80 to 95%. The transmittance of the aqueous solution is measured by spectrophotometry at 600 nm.

The following examples illustrate the present invention without, however, limiting the scope thereof.

EXAMPLES

Example 1

This example describes the preculture phases 1 and 2 for *Xanthomonas campestris*.

Preculture 1:
Composition of the preculture medium:

| | | |
|---|---|---|
| Yeast extract | 3 g/l | Oxoid |
| Malt extract | 3 g/l | Oxoid |
| Soybean peptone | 5 g/l | Oxoid |
| Sucrose | 10 g/l | Eurosucre |
| pH adjusted to 7 with $H_2SO_4$ | | |
| qsp 1 liter with drinking water | | |

All the constituents are dissolved in 1 liter of drinking water, homogenized by magnetic stirring and distributed into 500 ml Erlenmeyer flasks in 112 ml fractions.
The preparation is autoclaved for 30 minutes at 120° C.

The strain is initially stored in the form of tubes frozen at −196° C. by the process of freezing in liquid nitrogen vapors.

For liquid nitrogen freezing, a preculture is carried out on a specific medium having the following composition:

| | | |
|---|---|---|
| malt extract | 3 g | (obtained from Oxoid) |
| yeast extract | 3 g | (Oxoid) |
| soybean peptone | 5 g | (Oxoid) |
| glucose | 10 g | (obtained from Prolabo) |
| spring water qsp 1 l. | | |

For the preparation of the medium, all the ingredients are dispersed in spring water. The pH is adjusted to 6.5 with 10% $H_2SO_4$. The medium is sterilized for 20 minutes at 120° C., in an autoclave.

After incubation at 28° C. for 24 hours on a gyratory stirrer at 220 rpm and amplitude=50 mm, 10% by volume of pure sterile glycerol are added to the culture. The culture is then distributed into cryotubes of capacities varying from 1 ml to 10 ml, preferably from 2 ml to 4 ml.

These tubes are stored in liquid nitrogen vapor.

The preculture 1 is seeded with the aid of a cryotube previously thawed in ambient air. All or 50% of the cryotube is sterilely introduced into the 500 ml Erlenmeyer flasks, whose medium has been autoclaved and thus sterilized in the manner described above.

The medium seeded in this way is incubated for 24 hours at 28° C. on a gyratory stirrer at 220 rpm and an amplitude of 50 mm.

After 24 hours' incubation, we obtain a preculture whose pH varies from 7 to 7.5, whose viscosity is between 50 and 500 mPa.s and whose bacterial population of *Xanthomonas campestris* is greater than $10^{10}$/ml.

Preculture 2:
Preculture 1 is used to seed preculture 2.
Composition of the medium of preculture 2:

| | | |
|---|---|---|
| Sucrose | 10 g/l | Eurosucre |
| Carob germ flour | 4 g/l | Meyhall AG |
| $Na_2HPO_4$ | 3 g/l | Europhos |
| Drinking water or softened water qsp 1 l | | |
| pH adjusted with 10% sulfuric acid to 6.5 before sterilization. | | |

All the constituents are suspended in 1 liter of drinking water and the pH is adjusted to 6.5. The complete medium is autoclaved for 30 min at 120° C. after having distributed said medium into 500 ml Erlenmeyer flasks in 112 ml fractions.

These Erlenmeyer flasks are then seeded with 0.1 to 0.2 ml of preculture 1. These Erlenmeyer flasks are incubated for 24 to 30 hours at 28° C. on a gyratory stirrer at 220 rpm and an amplitude of 50 mm.

After 24 to 30 hours' incubation, we obtain a preculture whose pH varies from 5.8 to 7.1, whose viscosity is between 100 and 1000 mPa.s and whose bacterial population of Xanthomonas campestris is greater than $10^9$/ml.

Example 3

This example describes the preparation and the obtainment of the exopolysaccharide according to two fermentation processes, one with an organic nitrogen source and the other with a mixed organic nitrogen and inorganic nitrogen source.

In this example, two "preculture" steps are involved. These steps take place in 500 ml Erlenmeyer flasks, which corresponds to 100 ml of medium (see examples 1 and 2).

The production step, which corresponds to the step in the course of which the bacterial strain produces the polysaccharide, takes place in a 20 liter fermenter, of which 15 liters are useful.

Preculture step 1 and 2:

The preculture steps 1 and 2 are carried out in the same manner as in examples 1 and 2.

Production step:

Medium 1:

The last step is the step of production of exopolysaccharide.

The medium of fermenter 1 has the following composition:

| | | |
|---|---|---|
| sucrose | 42 g | Eurosucre |
| carob germ flour | 6 g | Meyhall AG |
| $MgSO_4.7H_2O$ | 0.25 g | Bittersalz |
| $Na_2HPO_4$ | 2 g | Prolabo |
| organic antifoam | 0.5 ml | |
| drinking or softened water qsp 1 l | | |

The preparation of the nitrogenous and the carbohydrate sources is carried out separately.

Sucrose→Qsp grams of glucose are dissolved in qsp 3 l of softened or drinking water in a Mariotte flask. The pH is lowered to 5.2 with 10% $H_2SO_4$. The solution is sterilized in a Mariotte flask for 45 minutes at 120° C. in an autoclave.

Carob germ flour+salts→Qsp g of carob germ flour, 30 g of $Na_2HPO_4$, 3.75 g of $MgSO_4.7H_2O$, and 7.5 ml of antifoam are dissolved in qsp 7 l of softened water. The pH is adjusted to 6 with 10% $H_2SO_4$. This mixture is sterilized in situ for 45 minutes at 120° C. 1N sodium hydroxide→40 g of NaOH pellets are dissolved in qsp 1 l of distilled water. The solution is sterilized in a Mariotte flask for 30 minutes at 120° C. in an autoclave.

When all the ingredients are at 28° C., they are mixed in the fermenter. The fermenter is then inoculated with qsp of preculture 2.

The fermentation conditions in the fermenter are as follows:

Stirring→200 rpm from 0 to 20 hours of age, then 400 rpm until the end of the fermentation Aeration→400 l/h from 0 to 18 hours then 825 l/h from 24 hours until the end of the fermentation The temperature is regulated at 28° C.

The pH is regulated at 6.8 with 1N NaOH.
The pressure is atmospheric pressure.
Medium 2:
Medium 2, which can be an alternative to medium 1, has the following composition:

| Sucrose | 42 g/l | (Eurosucre) |
|---|---|---|
| $NH_4NO_3$ | 1.15 g/l | (Atochem) |
| $MgSO_4.7H_2O$ | 0.25 g/l | (Bittersalz) |
| $(NH_4)_2HPO_4$ | 0.217 g/l | (Europhos) |
| Solubles of carob germ flour | 36 g/l | (Meyhall AG) |
| organic antifoam | 0.2 ml | |
| softened water qsp 1 l | | |

Sucrose→Qsp g of glucose are dissolved in qsp 3 l of softened water. The pH is adjusted to 5 with 10% $H_2SO_4$. The solution is sterilized in a Mariotte flask for 30 minutes at 120° C. in an autoclave.

Nitrogen+salts→17.25 g of $NH_4NO_3$, 3.75 g of $MgSO_4.7H_2O$, 3.22 gr of $(NH_4)2HPO_4$, 525 gr of solubles of carob germ flour and 3 ml of antifoam are dissolved in qsp 7 l of softened water. The pH of this solution is adjusted to 6 with 10% $H_2SO_4$. This mixture is sterilized in situ for 45 minutes at 120° C.

1N sodium hydroxide→40 g of NaOH pellets are dissolved in qsp 1 l of distilled water. The solution is sterilized in a Mariotte flask for 30 minutes at 120° C. in an autoclave.

The solubles of carob germ flour are prepared by dilution of flour to 6 to 15% in softened water. This solution can be untreated or treated with alkaline, acidic and/or neutral protease type enzymes; lipases; phytases; alkaline, acidic and/or neutral phosphatases; amylases; before being decanted, if desired, on a horizontal rotary decanter in order to eliminate the impurities which could interfere with the quality of the final product.

When all the ingredients are at 28° C., they are mixed in the fermenter (medium 1 or 2). The fermenter is then inoculated with qsp of preculture 2.

The fermentation conditions in fermenter 2 are as follows:
Stirring→200 rpm from 0 to 20 hours of age, then 400 rpm until the end of the fermentation
Aeration→400 l/h from 0 to 24 hours then 825 l/h from 24 hours until the end of the fermentation
The temperature is regulated at 28° C.
The pH is regulated at 6.8 with 1N NaOH
The pressure is atmospheric pressure or a pressure which can range from 0.5 to 4 bars.

Fermentation results:

According to the culture medium studied, the fermentation times vary from 45 to 65 hours, the dry matter precipitable with isopropanol varies from 20 to 30 g/kg, and the yield by weight with respect to the carbon source employed varies from 50 to 70%. The fermentation must obtained has a luminosity and a brightness never observed with any other source of nitrogen.

What is claimed is:

1. A process for producing exopolysaccharides comprising fermenting a microorganism that produces exopolysaccharides in a nutrient medium containing at least one carbon source assimilable by the microorganism and at least one organic nitrogen source, wherein said source comprises a fraction of a carob bean having a protein content of at least 45% by weight with respect to the dry weight of dry matter.

2. The process according to claim 1, wherein the protein content is of at least 60%.

3. The process according to claim 1, wherein the protein has a high content of arginine, of glutamine or glutamic acid, and of lysine.

4. The process according to claim 1, wherein the fraction of the carob bean has a content of lipids of at least 4% by weight with respect to the dry matter.

5. The process according to claim 4, wherein the content of lipids is of between 7 and 15%.

6. The process according to claim 1, wherein the fraction is a germ of the carob bean.

7. The process according to claim 1, wherein the carob bean fraction is in the form of a flour.

8. The process according to claim 7, wherein the flour has a granulometry of between 10 and 150 microns.

9. The process according to claim 1, wherein the nutrient medium further contains at least one inorganic nitrogen source.

10. The process according to claim 9, wherein the inorganic nitrogen source is an ammonium or sodium nitrate, an ammonium phosphate or sulfate, a magnesium sulfate, a potassium or sodium sulfate, or a mixture thereof.

11. The process of claim 1, wherein the organic and optionally inorganic nitrogen source In the fermentation medium is in a concentration of between 1 and 80 g/l.

12. The process according to claim 11, wherein the concentration of organic and optionally inorganic nitrogen source is of between 5 and 30 g/l.

13. The process according to claim 1, wherein the assimilable carbon source is a glucose or a sucrose.

14. The process according to claim 1, wherein the assimilable carbon source is a concentration of between 1 and 100 g/l.

15. The process according to claim 14, wherein the concentration of assimilable carbon source is of between 15 and 80 g/.

16. The process according to claim 1, wherein the fermentation of the microorganisms is carried out without an enzyme.

17. The process according to claim 1, wherein fermentation is carried out a temperature of between 15 and 100° C.

18. The process according to claim 17, wherein the temperature is of between 25 and 35° C.

19. The process according to claim 1, wherein the microorganism is selected from the group consisting of bacterias of the genus *Xanthomonas*, bacterias of the genus *Alcaligenes*, bacterias of the genus *Agrobacterium*, bacterias of the genus *Arthrobacter*, bacterias of the genus *Azotobacter*, bacterias of the genus *Pseudomonas*, bacterias of the genus *Corynebacterium*, bacterias of fungi of the genus *Sclerotium*, bacterias of the genus *Aspergillus*, and yeasts of the genus *Hansenula*.

* * * * *